United States Patent [19]

Sadar

[11] Patent Number: 5,747,667
[45] Date of Patent: May 5, 1998

[54] PARTICLE COUNTER VERIFICATION METHOD

[75] Inventor: Michael J. Sadar, Fort Collins, Colo.

[73] Assignee: Hach Company, Loveland, Colo.

[21] Appl. No.: 858,702

[22] Filed: May 19, 1997

[51] Int. Cl.[6] .................................................. G01N 15/02
[52] U.S. Cl. ............................................. 73/1.02; 356/243
[58] Field of Search ................................. 73/1.02, 1.03, 73/1.06, 865.5; 324/71.4; 356/243

[56] References Cited

U.S. PATENT DOCUMENTS 3,412,037  11/1968  Gochman et al. .
4,434,647   3/1984  Whitcomb et al. ................. 73/1.02
4,890,481   1/1990  Ezawa et al. ..................... 73/865.5

*Primary Examiner*—Robert Raevis
*Attorney, Agent, or Firm*—Dean P. Edmundson

[57] ABSTRACT

A method is described for rapid, simple and economical verification of the accuracy of the determination of an on-line particle counter without disconnecting it from a stream of liquid being tested. The method involves injecting a known volume of a liquid containing a known number and size of particles into the stream of liquid upstream from the detector. The number of particles displayed prior to injection of the known volume of liquid is compared with (1) the number of particles displayed after injection, and (2) the known number of particles which have been injected. No other modifications of the equipment is required, and only low volumes of test standard are used.

17 Claims, 6 Drawing Sheets

PARTICLE COUNTER VERIFICATION METHOD

FIELD OF THE INVENTION

This invention relates to particle counters. More particularly, this invention relates to particle counting apparatus and techniques for verifying the calibration of an on-line particle counter.

BACKGROUND OF THE INVENTION

Particle counting is the analytical science in which particles in a sample are both counted and sized. The sample medium can be either air or liquid (e.g., water). Historically, particle counting technology has been used in the pharmaceutical and semiconductor markets where the purity of the fluid is critical to producing a quality product. Most recently, particle counting is expanding into other markets, including water treatment (e.g., to monitor filter efficiency).

Particle counting technology as it applies to the water industry focuses on counting and sizing particles in the 2 to 400 micron range. However, the most specific range of interest can be further narrowed to the 2 to 20 micron range. This range is of interest because most waterborne pathogens are in the 2 to 20 micron range. Examples of such pathogens include cryptosporidium and giardia which have already caused numerous health problems in the U.S. and around the world. Particle counting does not exclusively count these pathogens, but it counts and sizes particles that have the same size characteristics as such pathogens.

The technology used to size and count particles is called light obscuration or light extinction measurements. In this technology, a fixed light source, typically a laser, projects a beam of light of constant intensity through a cross-section of a flowing sample. After the light passes through the sample it is projected onto a fixed detector. When a particle in the sample stream passes through the light beam, it casts a shadow on the detector because it reflects and/or absorbs some of the light beam (similarly as a shadow is cast by an object in front of the sun). This shadow on the detector causes a decreased response on the detector current that is able to be processed and analyzed. Thus, the larger the particle that passes through the detector, the larger the shadow and the larger the decreased response. By counting the pulses, software can count the number of particles passing through the sample and by analyzing the size of the pulse, the particles are sized (i.e., the smaller the pulse, the larger the particle). The information is then transferred to an output device that gives the number and sizes of the particles that are passing through the sample cell. One particle detected is called a count. Counts refers to the number of particles detected in the sample.

Light obscuration particle counting can further be divided into two sub-classes. These are volumetric and insitu particle counters. Volumetric counters count the entire cross section of the sample stream as it flows through the sample cell. In order to do this, the size of the sample cell must match the diameter of the laser beam, which typically results in a very small sample cell diameter. Volumetric counters can in theory count every single particle that passes through the sample cell. An in-situ particle counter does not count the entire cross section of a sample. Instead, the laser is focused to a very small area that is centered in the sample stream as it flows through the sample cell chamber. All particles in this "box" are then counted. In order to calculate the total number of particles in a sample, the volume of the box must be known and is typically between 10 and 20 percent of the total cross-section volume of the sample. Thus, a factor must be multiplied to the actual count number (referred to as raw counts) that is generated in an in-situ counter in order to accommodate counting for 100 percent of the sample stream. Each technique has its advantages and disadvantages.

There are several conditions and assumptions that are made in particle counting.

1. First, the sample flow rate must be consistent. If the flow rate varies, so will the rate of the number of particles that pass through the laser beam. Thus, results are generally normalized as counts per unit volume such as counts per mL (one count equals one particle).

2. It is assumed that only one particle flows through the sensor at one time. This is assumed to be true in clean and dilute samples, but as particulate matter increases, coincidence will occur. Coincidence is the condition in which the particulate level is high enough that more than one particle will pass through the sensor at the same time. This condition is falsely detected as a single, usually larger particle. Particle counters have been designed to reduce coincidence as much as possible. Coincidence is expressed as the coincidence limit, which is dependent on the manufacturer and begins to occur at particulate concentrations of between 10,000 and 20,000 particles per milliliter.

3. It is assumed that all particles are spherical and completely reflect light. In reality, particles are of a variety of shapes and the orientation of the particle as it passes through the laser beam is what defines its size.

4. It is assumed that particles are not transparent and cast complete shadows onto the detector. Many particles are transparent or semi-transparent (biological origin), in which only a fraction of the light is deflected and a less intense shadow is cast on the detector. The result is a smaller than expected response to the particle and under-sizing is the result. This is very common with biological particles in which their refractive index is very similar to water, and does cause a large attenuation of the incident light beam.

Particle counters are calibrated using particles of specific size, shape and known refractive index. Generally these materials are composed of styrene, polystrene or styrene divinylbenzene. These particles are all spherical with a very high refractive index which results in high reflectivity of the incident light beam (to cast the best shadow onto the detector). The standards are known as being mono-dispersed particles which simply means that they are of a very distinct size of a very small standard deviation about that size. The relationship of particle size to detector response is nonlinear in the 2 to 20 μm range, but is very linear above 20 μm. Thus, calibration of a particle counter in the 2 to 20 μm range is accomplished with multiple particle size standards which are defined by the manufacturer.

Due to the required electronics and the extremely critical orientation of the optical alignment of a particle counter, calibration of such instruments is an extremely complex procedure. This has made it impractical for calibrations to be performed by the end user, who generally neither possess the knowledge, methodologies, or equipment to properly calibrate such an instrument. Generally, in order to re-calibrate the instrument, it is taken off-line (removed from sample), sent back to the factory and then re-calibrated. This is a drastic upset to the monitoring environment in that either a replacement unit must be available to replace the instrument that is being calibrated, or monitoring of the sample ceases to occur due to the costs associated with obtaining a replacement particle counter. Further, the cost of re-calibration of a particle counter is extremely high and for many users, this is not an economically-favorable option. Thus, the creation of other options to particle counter calibration have been researched in recent years such as on-site calibration verification.

Calibration verification is generally a new concept in particle counting. The purpose of verification is to be able to test the performance of a particle counter in order to verify that the instrument is in or out of its calibration. The methods themselves need to be accurate and foolproof in order to give an accurate assessment of the state of the calibration of the test instrument. Verification is used to eliminate any uncertainty associated with an instrument. In an ideal situation, verification is to be performed on-site so that an instrument is off-line for a minimum amount of time. Calibration verification is designed to check a calibration and not change a calibration. Thus, the equipment used to verify a calibration is much more simplified and inexpensive than that which is required for calibration.

As mentioned above, calibration verification is a relatively new concept that has been mandated by its new user, i.e., the water industry. Thus, there are a few methods available and of these methods none are universally accepted. In the methods that are available, the instrument is taken off line in order to verify its performance. The verification process generally is of two types: sensor matching or verification against a standard. In sensor matching, a sample is run through two sensors, one known as the master and the other the test instrument. The data from the test instrument is compared to the master to determine if the calibration is valid. In the other method, a NIST traceable standard is drawn through the counter and analyzed. The instrument's analysis of this standard is compared to the stated values on the standard in order to validate the test instrument calibration.

Both of the above verification methodologies have encountered limited success, particularly with on-line particle counters. It is the purpose of this invention to provide an alternate methodology in which a count standard is used to verify the calibration of the particle counter. The method is intended to eliminate those problems associated with the above two methods, and at the same time provide better and more economical verification methodologies for in-line particle counters.

In the drinking water industry, particle counters are used to monitor filter efficiency. Specifically, particle counters are placed on the influent and effluent sides of a filter bed in order to monitor the efficiency of the filter. This monitoring also provides a surrogate method for determining microbial content in a finished water sample. By verifying that the sizes of suspected microbes are being filtered, one can assume the microbes themselves are also being filtered out. This is the other application purpose of particle counters in the water industry.

There is one drawback to using particle counters. Currently there is no simple procedure to use to verify the count and sizing accuracy of a particle counter. Those methods that are currently available are difficult, time consuming, and expensive.

The two most common methods of verifying the accuracy of a particle counter are count matching, and comparison to a count/size standard. Count matching involves matching several counters from a water plant to a single master counter. Typically, the master is a high accuracy volumetric counter. The problem with this method is the counter must be taken off-line and moved to the master counter to be verified. In addition, the master counter is an expensive instrument. This method has been demonstrated to work satisfactory, but does take a large amount of time to complete.

The use of a count standard to verify a particle counter accuracy is a fairly new technology. The typical method involves pulling a defined count and size standard through the counter via the use of a downstream pump for several minutes. The pump is downstream to prevent interference with the counter. Upstream pumps will introduce bubbles and vibrations which cause false positives during verification. Once the counts are stabilized, they are recorded and then compared to the theoretical values assigned to the count standard. The setup of this method is somewhat cumbersome and does consume a significant amount of standard. These count/size standards are relatively expensive and therefore the verification of several counters can be expensive. This methodology works best on low volume extinction counters. However, when in-situ counters are used, where flow rates run 150–500 mL/minute, this becomes an impractical method.

There has not heretofore been provided a rapid, simple and economical method for verifying the accuracy of the determination of an on-line particle counter.

SUMMARY OF THE PRESENT INVENTION

In accordance with the present invention there is provided a method for simply verifying the accuracy of the determination of an on-line particle counter without disconnecting it from a stream of liquid being tested. The method involves the steps of:

(a) injecting a known volume of a liquid containing a known number and size of particles into the stream of liquid upstream from the particle counter detector within a defined period of time;

(b) observing the number of particles detected and displayed by the particle counter; and (c) comparing the displayed number of particles prior to injection of the known volume of liquid with (i) the displayed number of particles after injection, and (ii) the known number of particles injected.

The method of the invention is very simple and rapid. It is also repeatable and affordable. No previous method has these advantages.

Other advantages of the present invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

The method of this invention involves injecting a known or defined volume of a test standard containing a known number and size of particles into the stream of liquid entering the on-line particle counter. The known volume is injected into the liquid stream at a point which is upstream from the particle counter detector within a defined period of time. Based upon the known or defined volume of test standard injected, the total counts of each size of particle can be calculated and compared to the instrument's response to the injection of the standard.

For practicing the method of this invention it is not necessary to have specialized equipment. Rather, inexpensive, off-the shelf components can be used, e.g., a graduated syringe, plastic tubing, a valve and Leur-lock connectors.

Also, the test standard which is used can be any commercially-available liquid standard which contains a known number and size(s) of particles. The volume of test standard which is used for each injection or test is typically (but not limited to) in the range of about 2 to 5 mL.

The point at which the test standard is injected into the on-line system to be tested is important. The injection point should be as close to the laser sensor (i.e., particle detector) as possible while assuring that the test standard is evenly mixed with the liquid in the sample stream by the time that it reaches the particle detector.

A particularly preferred manner of injecting the test standard into the liquid stream leading to the particle counter has been found to be by means of injecting the standard directly into a 90° elbow 10 in the line 12 bringing liquid into the particle counter 14 for testing. The elbow 10 is immediately upstream from the particle counter and in close proximity to it. This is illustrated, for example, in FIGS. 1, 2, 5 and 6.

Figure 1:
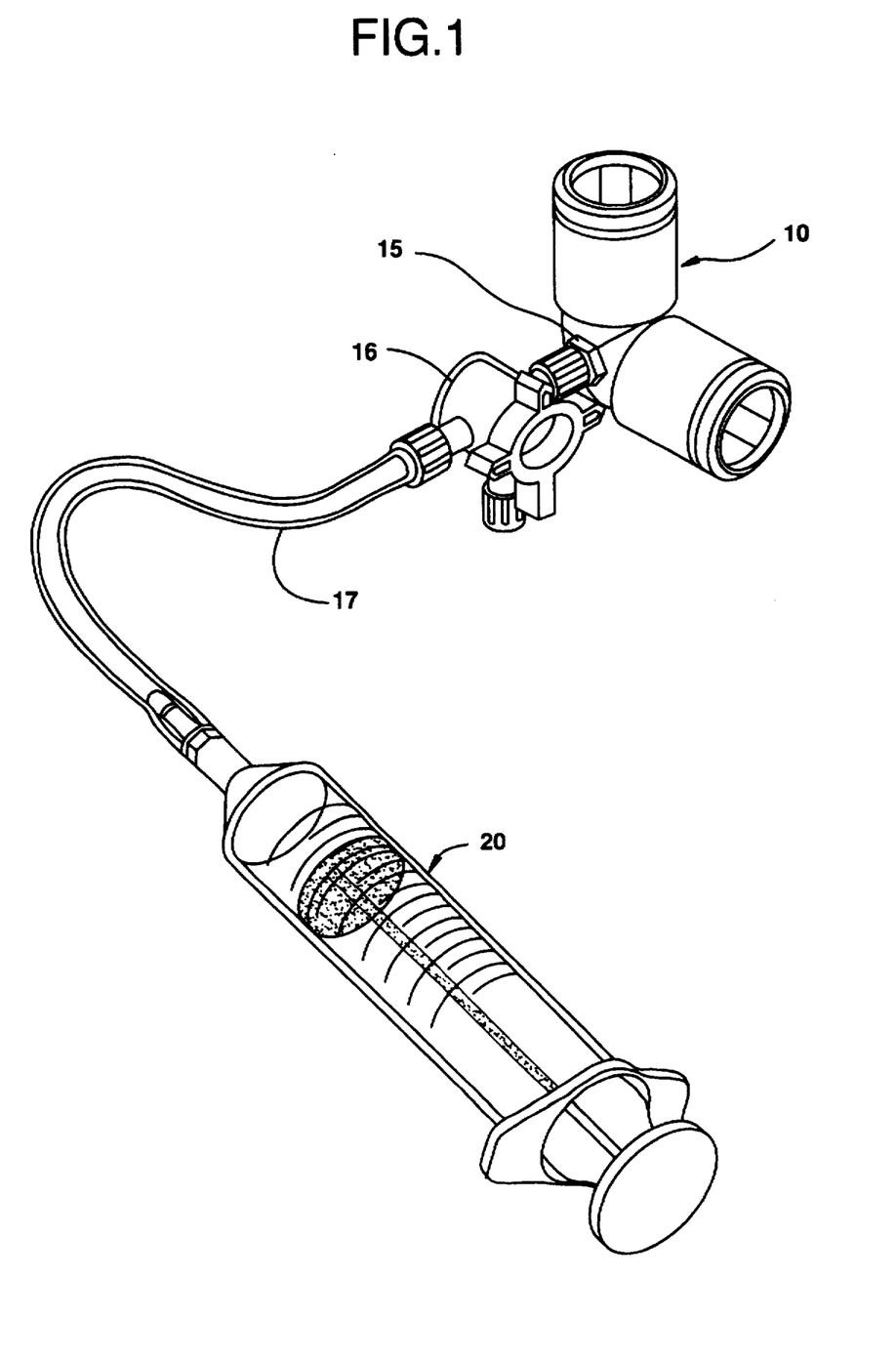
FIG. 1 is a perspective view illustrating one embodiment of the invention.
Figure 2:
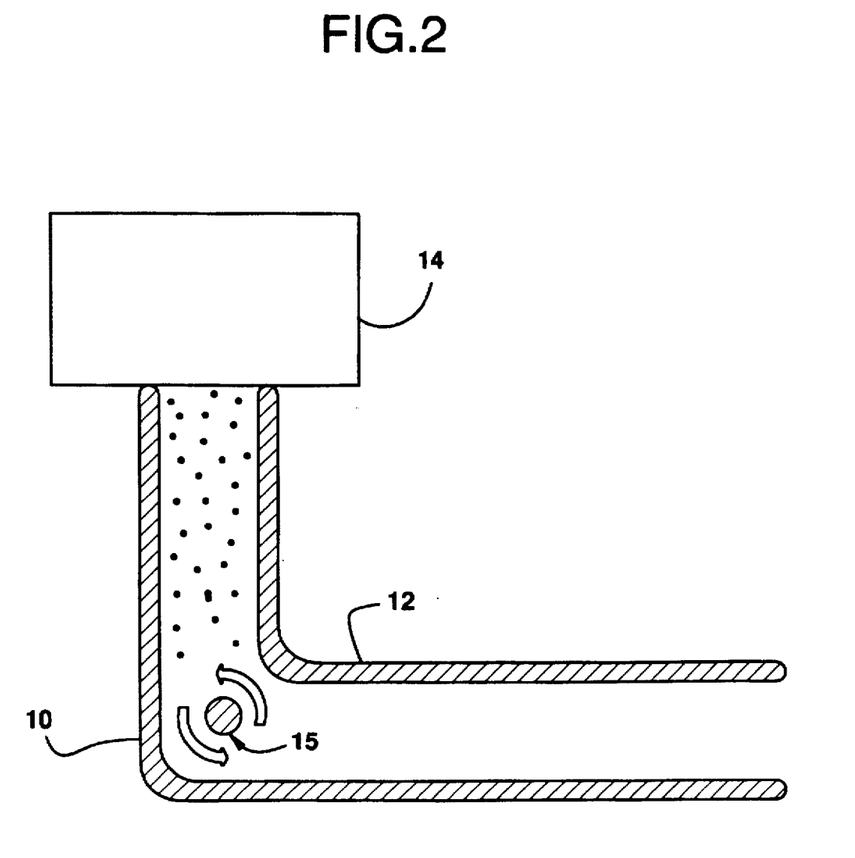
FIG. 2 is a cross-sectional view of the liquid inlet line shown in FIG. 1.

The test standard is a liquid which is contained in graduated syringe 20 which is connected through feed line or tube 17, then through valve 16, to an inlet port 15 in the side of the elbow 10, as shown. When the valve 16 is open, a defined amount of the test standard can be injected from the syringe directly into the elbow 10 where the liquid flow is most turbulent and very good mixing of the test standard with the liquid stream takes place. This valve allows for the backflushing of the verification injection system. The cleanliness of the injection system is very important in relation to the verification method's performance. This valve provides a permanent and simple means of cleaning this portion of the injection system.

The tubing 17 attaches the syringe 20 to the injection port 15 that is on the particle counter. This tubing is to be made of a material such that it is easily cleaned and does not have an affinity to nor an attraction to particles, charged or uncharged. This tubing is to provide a flexible connection between the syringe and the particle counter. It allows the user to position the syringe so the injection can be made consistently and easily. This also allows the user, to ergonomically position one's self so that the syringe can be viewed an angle such that the measurement graduations can be easily read. This again will lead to improved accuracy and reproducibility with the procedure of this invention.

The flexible tubing 17 also provides a dampening of vibrations between the user and the particle counter. If the syringe was connected to the particle counter directly or with a rigid tube or conduit, vibrations from the user would be easily transferred to the particle counter apparatus. These vibrations would in-turn dislodge particulate matter and/or bubbles that would otherwise remain attached to the insides of the counter. This released particulate matter would then be detected as false positive counts.

The rate of injection of the test standard into the sample liquid stream is also important in being able to obtain an accurate calibration verification. The test standard should be injected at a rate slow enough such that no air bubbles are drawn into the sample line. Also, the rate of injection should not be at such a fast rate that "coincidence" occurs (i.e., masking or shadowing of one particle by another in front of the detector). However, the injection should be sufficiently rapid that the background of the sample liquid stream remains constant. Further, the rate of injection must be sufficient to allow all of the particles in the added test standard liquid to be counted in one count cycle of the particle counter.

The count cycle defines the length of time that the sample stream is to be analyzed before tallying and expressing the results. These results are expressed as counts (number of particles) per unit volume. Further, volume is a function of flow rate which passes through the particle counter and is a function of time. In order for results to be accurate and consistent, the flow through the counter must also be consistent and therefore is fixed at a constant rate that cannot be changed on on-line particle counters. Thus, counts are determined by dividing the total number of counts detected in a specified time frame by the time taken to collect all of these counts. Since time is directly related to volume, the counts per unit time are easily converted to counts per unit volume.

Cycle times vary according to sample, software, and data transmission utility. Typically, cycle times range from 30 seconds to 10 minutes, and currently 1 minute is the standard. This makes it easy to relate to volume, since it is generally defined as mL/minute. Thus, every minute a defined number of mL of sample passes through the sensor, and the calculation to determine the number of particles counted per mL of sample becomes an easy mathematical calculation.

When using the method of this invention to verify the performance of a particle counter, it is very important for all of the test particles to be injected and counted during the same count cycle. If this does not occur, then only a portion of particles will be counted during the cycle and the remainder of these particles will be counted on the successive cycle. Thus, only a fraction of the particles will be counted during the cycle when the injection was performed and the rest are lost. This leads to substantial negative error due to loss of counts during the test cycle.

Figure 3:
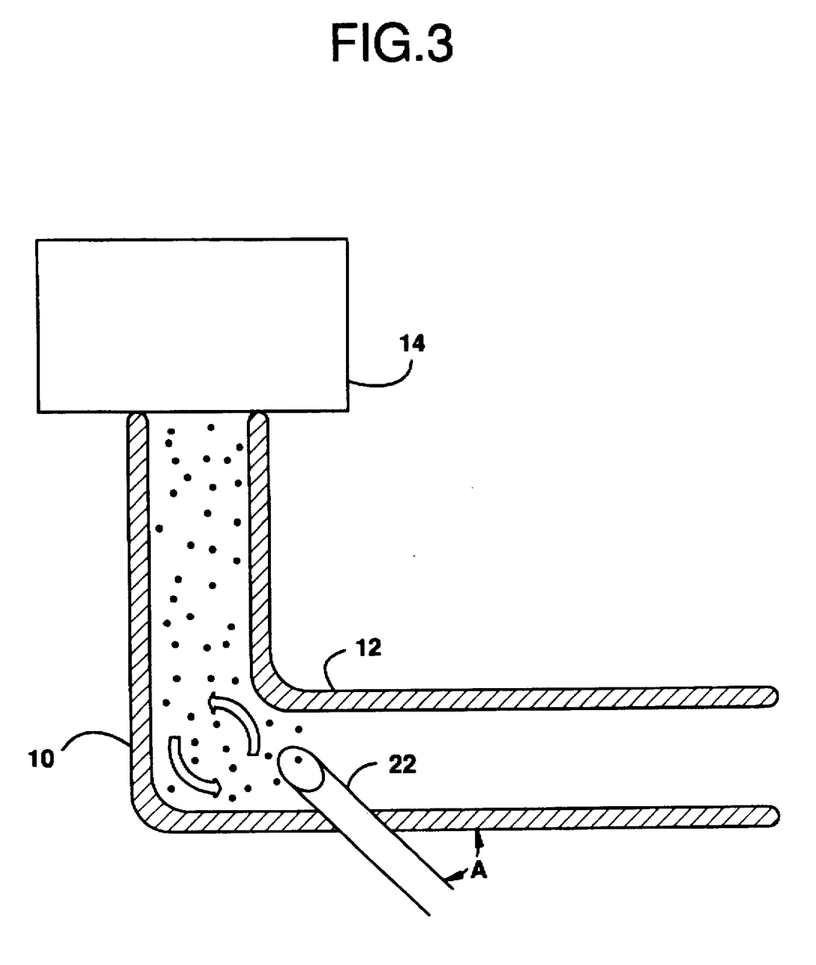
FIG. 3 is a cross-sectional view of a liquid inlet line showing another type of injection port for a test standard.

Another manner of injecting the test standard into the flowing sample stream is illustrated in FIG. 3. In this embodiment the injection is made at an angle A to the liquid stream such that the test standard is directed out of the injection tube 22 in the downstream direction. Preferably the angle A is less than 90° (and more preferably is in the range of about 0° to 45°). Injection of the test standard immediately upstream from (e.g., within about 24 inches), or within, elbow 10 is preferred.

Figure 4:
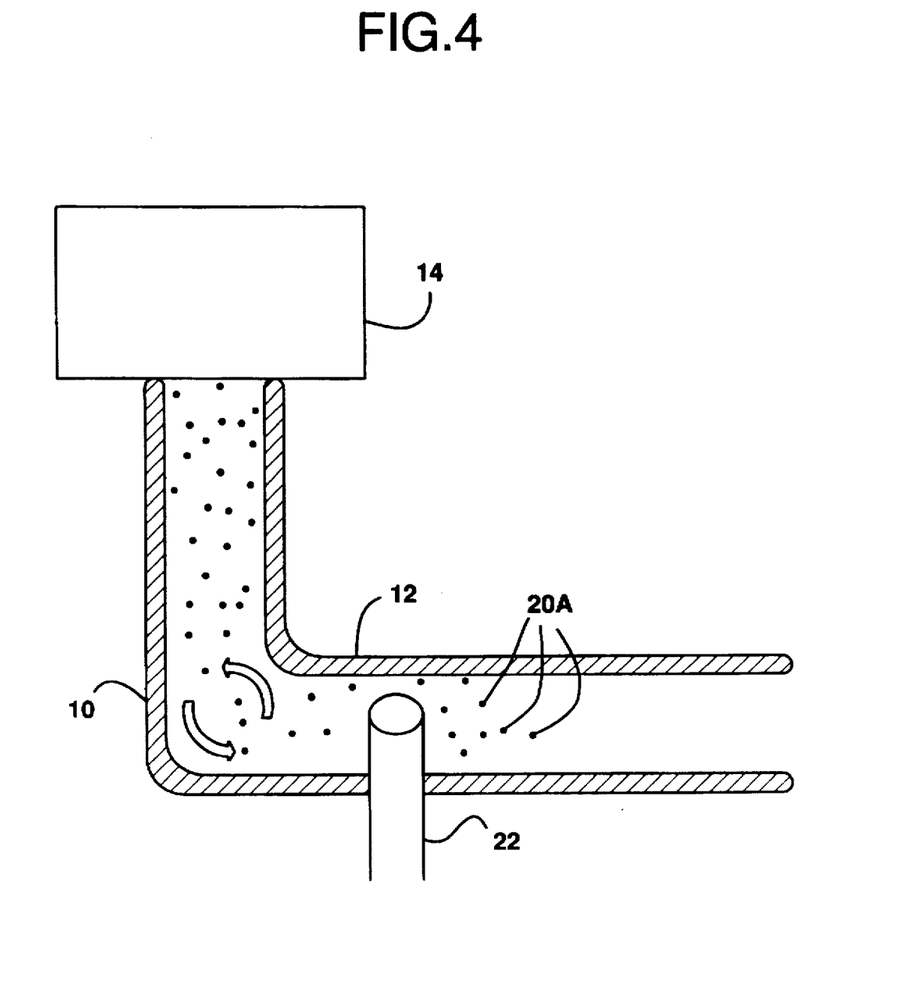
FIG. 4 is a cross-sectional view of a liquid inlet line showing another type of injection port for a test standard.

FIG. 4 illustrates injection of the test standard into the sample stream at a 90° angle to the stream. In this embodiment, some of the added particles are forced in an upstream direction as shown. Although this is not necessarily unworkable, it does increase the chance that some of the particles in the test standard may not be pushed through the particle counter within a single counting cycle, depending upon the rate of injection and the distance between the injection site and the particle detector.

The injection point location must be such that it allows for the particles to completely pass through the sensor in the same cycle. Thus, the closer the injection port is to the sensor, the shorter the cycle time can be. Conversely, the farther the injection port is from the sensor, the longer it takes for all of the particles to pass through the sensor and the longer the cycle time must be to accommodate this. Thus, the ideal case is to have the injection port be as close to the sensor as possible to minimize the cycle time, but at the same time must be far enough away from the sensor to allow for adequate and thorough mixing of the count standard with the sample stream.

If the test standard is injected too far upstream from the particle counter, or if it is injected in a manner such that the added particles are dispersed through too great a volume of the liquid stream, then there is greater risk that some of the added particles will not be counted in a single count cycle of the particle counter. Consequently, it is preferred to add the test standard to the liquid stream in close proximity to the particle counter (e.g., within a few inches) and in a time period less than or equal to the count cycle time.

The method of the invention is preferably used with short cycle times. The probability of the carrier stream changing during the verification process decreases as the counter cycle time decreases.

Figure 5:
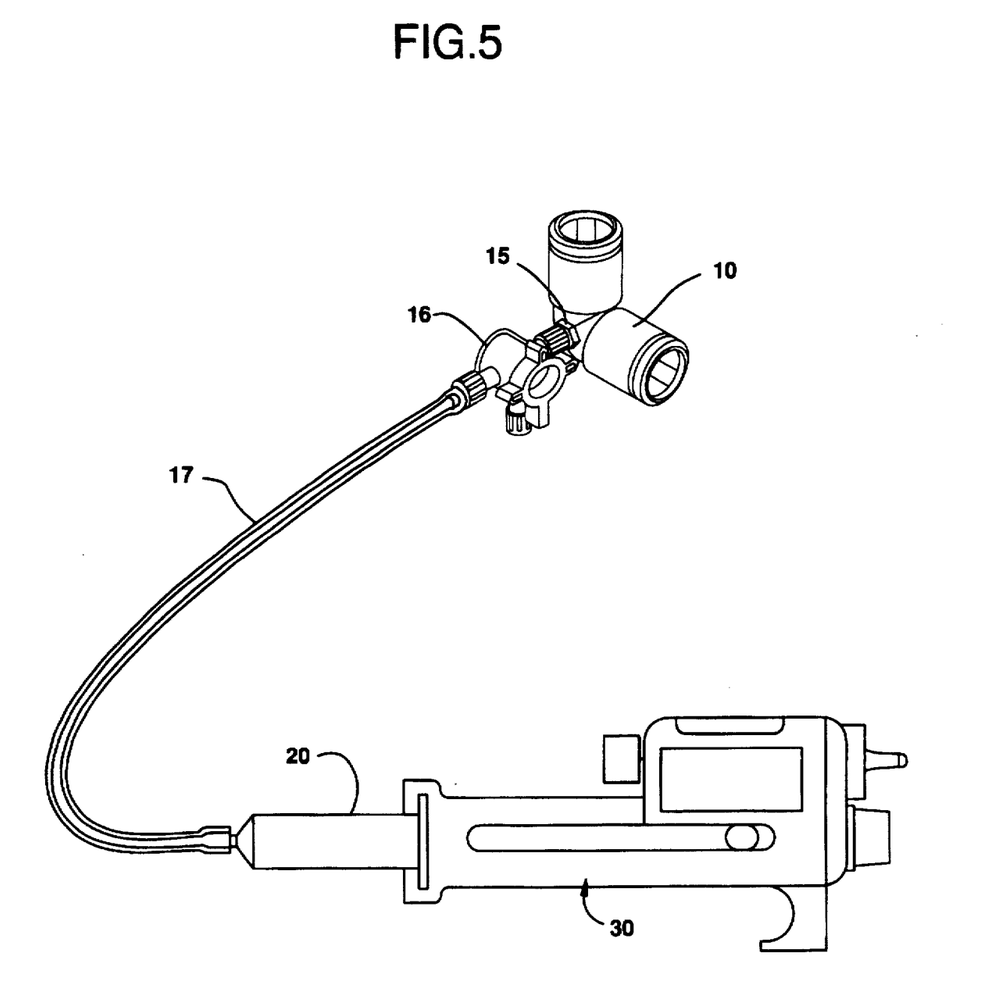
FIG. 5 shows the use of a digital titration device for injecting a test standard.
Figure 6:
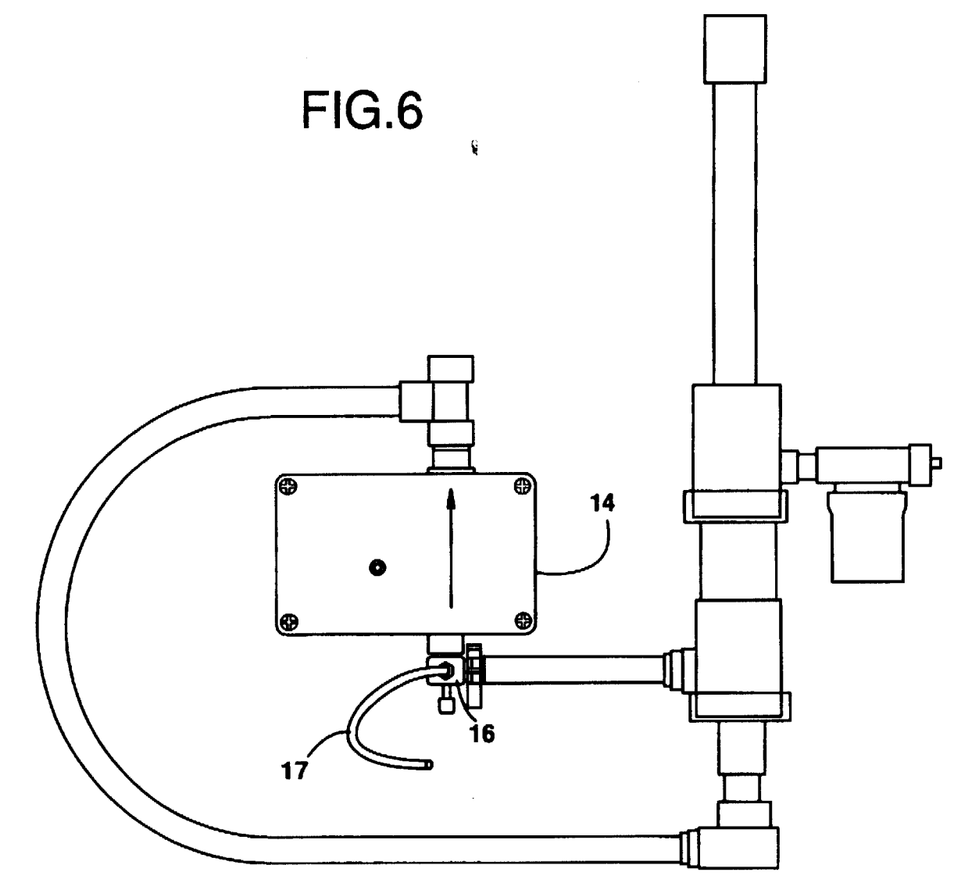
FIG. 6 is a side elevational view of a particle counter system in which the embodiment of FIG. 1 is used.

FIG. 5 shows the use of a conventional digital titrator device 30 for effecting very simple and accurate injection of a test standard into the flow line for the liquid stream being tested.

The use of this apparatus in conjunction with the verification procedure allows the user to focus in the count range of interest. This instrument does provide rapid, accurate and reproducible low volume injections that can be easily customized to fit in the same count range as that of the sample. This typically cannot be accomplished because count efficiency is defined using higher count concentrations. High count concentrations are used because 1) it is difficult (and expensive) to produce low count standards due to analysis and contamination issues in production; and 2) the volumes injected during verification are typically much higher (one to several hundred mL per injection) . The digital titrator allows usage of this verification method on low-volume counters such as light extinction counters that typically have flow rates that are <100 mL/minute. Further, since this apparatus injects very small volumes of the count standard, the consumption of such standards is reduced. Also, the use of small volume injections reduces the probability of particle coincidence occurring due to injection. It allows precise reproducible injections of low level counts. It allows for manual injection volumes of standards that can be varied according to conditions of sampling.

The quality of the sample stream is important. Preferably the stream should be low in particles (which is typical of effluent water at a water treatment plant). However, influent water may include so many particles that counts may be at or near the coincident limit. In such an event, the influent water may not be suitable for carrying the test standard particles through the counter. In the situation where the carrier stream is too high in particle counts, either the effluent water should be used or a filter may be placed in the stream prior to the injection point in order to eliminate the residual counts.

In either case, of using effluent or filtered water as the carrier stream for the particle count standard, background counts should be run before and after the injections of the standard. These counts can be averaged together and then subtracted from the total standard counts. Running background counts before and after the injections also validates that the carrier stream remains constant during the validation.

Specifically, the verification procedure involves the following steps:

(1) Assembly of the injection apparatus;
(2) Preparation of the count/size standard;
(3) Setup of the particle counter software for validation;
(4) Preparation of the carrier stream water-using effluent or filtered water; for high count liquids a sub-micron filter is installed to remove particles that would cause false positives;
(5) Allowing the counter to clean out and stabilize with the carrier stream;
(6) Running background counts, injection of the standard multiple times, followed by repeating the background counts.
(7) Calculating the size and number of counts detected versus the number of known counts injected into the counter.

Other variants are possible without departing from the scope of this invention.

What is claimed is:

1. A method for verifying the accuracy of the determination of an on-line particle counter without disconnecting it from a stream of liquid being tested, wherein the particle counter includes a detector capable of producing a display signal in response to the presence of a particle present in the liquid stream flowing past said detector, the method comprising the steps of:

(a) injecting a known volume of a liquid containing a known number and size of particles into said stream of liquid upstream from said detector within a defined period of time;
(b) observing the number of particles detected and displayed by said particle counter; and
(c) comparing the displayed number of particles prior to injection of said known volume of liquid with (i) the displayed number of particles after said injection, and (ii) the known number of particles injected.

2. A method in accordance with claim 1, wherein said liquid stream passes through a conduit including an elbow prior to passing through said particle counter, and wherein said known volume of liquid is injected into said liquid stream at said elbow.

3. A method in accordance with claim 2, wherein said elbow is within about 20 inches of said particle counter.

4. A method in accordance with claim 2, further comprising an inlet valve in said elbow, wherein said inlet valve is movable between open and closed positions.

5. A method in accordance with claim 2, wherein said known volume of liquid is injected into said stream from a syringe.

6. A method in accordance with claim 1, wherein said known volume of liquid is injected into said stream of liquid by means of a digital titrator device.

7. A method in accordance with claim 1, wherein said known volume of liquid is injected into said liquid stream within about 24 inches of said particle counter.

8. A method in accordance with claim 7, wherein said known volume of liquid is injected into said liquid stream at an angle such that said known volume of liquid is projected into the downstream direction of said liquid stream.

9. A method in accordance with claim 1, wherein said defined period of time is not greater than the cycle time of said particle counter.

10. A method for verifying the accuracy of the determination of an on-line particle counter without disconnecting it from a stream of liquid being tested, wherein the particle counter includes a detector capable of producing a display signal in response to the presence of a particle present in the liquid stream flowing past said detector, wherein said particle counter displays the number of particles counted in a defined cycle time, the method comprising the steps of:

(a) injecting a known volume of a liquid containing a known number and size of particles into said stream of liquid upstream from said detector within a defined period of time which is not greater than said cycle time;

(b) observing the number of particles detected and displayed by said particle counter; and (c) comparing the displayed number of particles prior to injection of said known volume of liquid with (i) the displayed number of particles after said injection, and (ii) the known number of particles injected.

11. A method in accordance with claim 10, wherein said liquid stream passes through a conduit including an elbow prior to passing through said particle counter, and wherein said known volume of liquid is injected into said liquid stream at said elbow.

12. A method in accordance with claim 11, wherein said elbow is within about 20 inches of said particle counter.

13. A method in accordance with claim 11, further comprising an inlet valve in said elbow, wherein said inlet valve is movable between open and closed positions.

14. A method in accordance with claim 11, wherein said known volume of liquid is injected into said stream from a syringe.

15. A method in accordance with claim 10, wherein said known volume of liquid is injected into said stream of liquid by means of a digital titrator device.

16. A method in accordance with claim 10, wherein said known volume of liquid is injected into said liquid stream within about 24 inches of said particle counter.

17. A method in accordance with claim 16, wherein said known volume of liquid is injected into said liquid stream at an angle such that said known volume of liquid is projected into the downstream direction of said liquid stream.

* * * * *